United States Patent
Prins et al.

(10) Patent No.: US 7,106,051 B2
(45) Date of Patent: Sep. 12, 2006

(54) MAGNETORESISTIVE SENSING DEVICE, SYSTEM AND METHOD FOR DETERMINING A DENSITY OF MAGNETIC PARTICLES IN FLUID

(75) Inventors: Menno Willem Jose Prins, Eindhoven (NL); Reinder Coehoorn, Eindhoven (NL)

(73) Assignee: Koninklijke Philips Electronics, N.V., Eindhoven (NL)

( * ) Notice: Subject to any disclaimer, the term of this patent is extended or adjusted under 35 U.S.C. 154(b) by 37 days.

(21) Appl. No.: 10/498,952

(22) PCT Filed: Dec. 18, 2002

(86) PCT No.: PCT/IB02/05599
§ 371 (c)(1),
(2), (4) Date: Jun. 16, 2004

(87) PCT Pub. No.: WO03/054566
PCT Pub. Date: Jul. 3, 2003

(65) Prior Publication Data
US 2005/0035757 A1    Feb. 17, 2005

(30) Foreign Application Priority Data
Dec. 21, 2001 (EP) .................... 01205092

(51) Int. Cl.
G01N 27/74 (2006.01)
G01N 27/72 (2006.01)
G01R 37/12 (2006.01)
G01B 7/00 (2006.01)

(52) U.S. Cl. .................. 324/204; 324/228; 324/244
(58) Field of Classification Search ............... None
See application file for complete search history.

(56) References Cited

U.S. PATENT DOCUMENTS 5,981,297 A * 11/1999 Baselt ................. 436/514
2004/0115786 A1 * 6/2004 Laing ................. 435/199

* cited by examiner

Primary Examiner—Bot LeDynh (57) ABSTRACT

The present invention relates to a magnetoresistive sensing device, a system and a method for determining a density of magnetic particles in a fluid. The magnetoresistive sensing device has a substrate (1) with a layer structure (2) for supporting a fluid (3). The layer structure has a first surface area (4) in a first level and a second surface area (5) in another second level and a magnetoresistive element (6) for detecting the magnetic field of at least one magnetic particle (7) in the fluid, the magnetoresistive element being positioned near a transition (8) between the first and second surface area and facing at least one of the surface areas. A corresponding system and method is described as well.

19 Claims, 4 Drawing Sheets

MAGNETORESISTIVE SENSING DEVICE, SYSTEM AND METHOD FOR DETERMINING A DENSITY OF MAGNETIC PARTICLES IN FLUID

The invention relates to a magnetoresistive sensing device.

The invention also relates to a system for determining a density of magnetic particles in a fluid comprising the magnetoresistive sensing device.

The invention further relates to a method for determining a density of magnetic particles in a fluid using the magnetoresistive sensing device.

Chemla et al. describe in the article "Ultrasensitive magnetic biosensor for homogeneous immunoassay", PNAS, Dec. 19, 2000, vol. 97, no. 26 a SQUID based sensor of supermagnetic particles. The SQUID detects the magnetic flux due to magnetic nanoparticles that are present in zone on a substrate, in a well in the surface. A Mylar® sheet to which the particles are attached so that they are immobilized, which fits in the well, is described as an example thereof. An in-plane magnetic field is applied to induce magnetic moments of the magnetic nanoparticles. Then the field is switched off. The subsequent relaxation of the magnetic dipoles of the attached nanoparticles according to the Néel mechanism produces a measurable time dependent field perpendicular to the plane of the immobilised zone for a period of several seconds. This field is detected by a SQUID probe placed close to the immobilised zone.

Nanoparticles in the bulk liquid are free to rotate according to Brownian motion. In the systems studied by Chemla et al. the relaxation of the magnetic field due to this rotation is much faster than that of the immobilized particles. Therefore, the overall magnetic flux in the SQUID sensor produced by these non-immobilized particles in the fluid is almost immediately reduced to zero.

A drawback of the known device resides in that the SQUID operates only at cryogenic temperatures. The accurate positioning of the SQUID with respect to the immobilized zone is difficult, and the choise of substrates is limited due to their small required thickness.

A major disadvantage of the known device is that it is not possible to determine the volume concentration of magnetic particles in the fluid due to the fast relaxation of the magnetic nanoparticles in the bulk fluid after the magnetic field has been turned off. There is a general need for a very accurate determination of the density of biological molecules or molecular fragments, which are further called the "target". It is therefore necessary that the density of magnetic particles functioning as magnetic labels to a target can be determined with very high accuracy. It would be of general interest to have an accurate system and method for the determination of the volume density of magnetic particles in the fluid.

The introduction of micro-arrays or biochips is revolutionising the analysis of DNA (desoxyribonucleic acid), RNA (ribonucleic acid) and proteins. Applications are e.g. human genotyping (e.g. in hospitals or by individual doctors or nurses), bacteriological screening, biological and pharmacological research. Nowadays, there are many types of assays used to analyze small amounts of biological molecules or molecular fragments, such as a binding assay, competitive assay, displacement assay, sandwich assay or diffusion assay. The challenge in biochemical testing lies in the low concentration of target molecules (e.g. fmol.l$^{-1}$) that has to be determined in a fluid sample with a high concentration of varying background material (e.g. mmol.l$^{-1}$). The targets can be peptides, hormones biomarks like myoglobine, proteins, nucleic acids, steroids like cholesterol, enzymes, antigens, haptens or drugs. The background material or matrix can be urine, blood, or serum. Other important tests are cell counting, biological coaggulation and biological activity.

Labels improve the detection limit of a target. Examples of labels are optical labels, colored beads, fluorescent chemical groups, enzymes, optical barcoding or magnetic labels.

It is therefore necessary that the volume density of magnetic particles in a fluid functioning as magnetic labels to a target can be determined with very high accuracy.

It is an object of the present invention to provide a system of the type mentioned in the openings paragraph, which is able to determine the volume density of magnetic particles in the fluid.

The object of the invention regarding the system in accordance with the invention is achieved in that the magnetoresistive sensing device comprises a substrate with a layer structure for supporting a fluid, the layer structure having a first surface area in a first level and a second surface area in another second level and a magnetoresistive element for detecting the magnetic field of at least one magnetic particle in the fluid, the magnetoresistive element being positioned near a transition between the first and second surface area and facing at least one of the surface areas. The fluid comprises a liquid or a gas.

The magnetoresistive sensing device detects the net magnetic moments of magnetic particles. Magnetic particles being in the fluid and on the layer structure have a magnetic moment m. The magnetic moments are aligned with a magnetic field, applied perpendicular to the magnetoresistive sensing device. When the substrate would have been planar, the net magnetic field in the plane of the magnetoresistive element in the substrate, due to randomly dispersed nanoparticles in the bulk of the fluid, would average out to zero. However, due to the transition, there is a magnetic fringing field. The planes of the first and second surface areas are not necessarily parallel to each other. They can make an angle with each other. The surfaces are not necessarily flat. The transition may have a gradient profile. Transitions next to each other may form a wave-like surface, whereby the first surface area and second surface area can be extremely small.

In general the in plane magnetic field in the magnetoresistive element can be derived by integration. Just for illustrative purposes the expression for determining the volume density is given for a transition being a step from the first to the second surface areas. Due to the stepped structure of the surface, the distance $d_1$ from the magnetoresistive sensing device to the first surface area is different from the distance $d_2$ to the second surface area. There is a net magnetic field in the plane of the magnetoresistive sensing element, and just underneath the edge between the surfaces at the first and second level $$H_x \approx -\frac{m}{2\pi}\left[N \ln\left(\frac{d_2}{d_1}\right)\right],$$

wherein N is the volume density is of magnetic particles in the fluid, m is the magnetic dipole moment per particle, and wherein x is the in-plane direction that is perpendicular to the step edge. The positive x-direction is the direction from the area with distance $d_1$ to the area with distance $d_2$.

The magnetoresistive sensing device transforms the magnetic field in a resistance value. Because the resistance versus magnetic field of the magnetoresistance device is well known, the volume density can be calculated from the resistance value.

For calibration purposes, the resistance versus magnetic field in a fluid without magnetic particles should be measured. The magnetoresistive sensing device can be based on e.g. the GMR, TMR or AMR effect. The magnetoresistive sensing device comprises a layer structure of thin films, preferably with a linear resistance versus magnetic field curve, especially for small magnetic fields, and with a negligible hysteresis.

Preferably there is an overlap between the magnetoresistive sensing element and the first surface area in the case of a substantially perpendicular projection of the first and second surface area surface on the magnetoresistive sensing device.

The net magnetic field generated by the magnetic particles at the transition between the first and the second surface area is strongest. Especially in the case of a sharp transition between the layers at the first and second level, the in-plane magnetic field in the magnetoresistive sensing device is in a first order approximation $$H_x(x) \approx -\frac{mN}{2\pi} \int_{d_1}^{d_2} dz \left[\frac{z}{x^2 + z^2}\right], \quad (2)$$

wherein the x is the distance defined with respect to the center of the transition, along the direction perpendicular to the step edge direction and parallel to the first surface. The magnetic field that has to be detected is strongest when the magnetoresistive sensing device is present close to transition and has a short distance to the first surface.

Preferably, the transition between the first and the second surface area has a step-like profile. The equation (2) is a first order approximation for this situation.

Generally there is also an areal density of magnetic particles present on the structured surface. The a real density of the magnetic nanoparticles on the first surface is given by $\sigma_1$, and the areal density on the second surface is given by $\sigma_2$. The volume density of magnetic nanoparticles in the fluid containing the with nanoparticles labeled elements is given by N. For a particle magnetisation along the positive z-direction, the in-plane magnetic field below the surface step can to first order be approximated by:

$$H_x \approx -\frac{m}{2\pi} \left[\frac{\sigma_1}{d_1} - \frac{\sigma_2}{d_2} + N \ln\left(\frac{d_2}{d_1}\right)\right] \quad (3)$$

with m the magnetic moment of the particle. The areal particle density typically ranges between zero and $10^3$ to $10^4$ particles per $\mu m^2$.

The volume density can be calculated from a combination of the unequal output signals of several unequal magentoresistive sensing devices, as explained below.

If the areal density on the first surface is unequal to the second surface, the areal densities and volume density can be determined from the structured surface, having at least three structures with an unequal combination of depths $d_1$ and $d_2$. The surface structures each have an identical magnetoresistive sensing device, being present in the same plane, at the same position relative to the each step. Due to the different heights of the steps, the three different output signals from the sensing devices make it possible to derive the surface area1 density and the concentration of magnetic particles. In the special case in which the areal densities at the first and second surfaces are equal the areal and volume density can be determined from a structured surface, having at least two structures with an unequal combination of depths $d_1$ and $d_2$.

In a binding assay, a competition assay, or a displacement assay, generally there is a probe area present on the first surface area. Attached to the probe area are binding sites.

In a binding assay, the magnetic particles are coupled to a target forming magnetic labels. The magnetic labeled target diffuses through the fluid by Brownian motion. Small particles diffuse faster and reach the binding sites faster than large particles. The magnetic labeled target is bound at the binding site.

In a competition assay, there are targets of which the concentration is to be determined and magnetically labeled targets present in the fluid. The two species compete for binding to capture molecules. Differences in abundance and binding kinetics (diffusion, binding efficiency) determine the relative binding of the species to the capture molecules. The more magnetically labeled target is present at the binding sites, the less target was present in the test volume.

In a displacement assay magnetic labeled targets are bound at the binding sites. Target in the volume diffuses to the binding sites and replaces the magnetic labeled target molecules. The larger the concentration of target in the fluid, the less magnetic labeled target is detected.

As given by equation (3), a determination of the volume density of magnetic particles N requires that the effect of the areal density of magnetic particles on the surfaces at levels one and two is eliminated.

The detection accuracy can be improved when the magnetoresistive sensing device has a Wheatstone bridge configuration comprising magnetoresistive elements being positioned on the substrate. The first bridge-half may be located below a first transition between the a first surface area and a second surface area, and the other bridge-half being located below a second, dissimilar, transition between surface areas, such that the changes of the resistances of the two sensors, upon the application of the external field, are different.

The detection accuracy can further be improved when the pairs of first and second magnetoresistive sensing devices or groups of first and second magnetoresistive sensing devices are used, each pair being associated with and located with a transition, the outputs of the first and second magnetoresistive devices being fed to means for detecting a change in resistance of the magnetoresistive sensing devices upon the application of the external field.

In an advantageous embodiment, the layer structure is formed by a plurality of grooves, positioned parallel to each other. The magnetoresistive sensing elements are made of a material of which the resistance versus field curve is to a first approximation a linear function of the x-component of the applied field. The elements are present in the substrate and are substantially stripe-shaped and centered along the edges of the grooves. The distance between the groove edges is larger than the width of the stripe shaped magnetoresistive elements.

In a second advantageous embodiment, the layer structure is also formed by a plurality of grooves, positioned parallel to each other. However, the magnetoresistive sensing elements are now made of a material of which the resistance versus field curve is to a first approximation a symmetric function of the x-component of the applied field. It is only sensitive to the absolute value of the x-component of the field, and not to its sign. The elements are present in the substrate and can have a dimension in the x-direction that is much larger than the distance between the edges between the grooves. In that case the precise position of the grooves with respect to the element is not of a critical importance. Alternatively, when the dimension of the magnetoresistive stripe-shaped elements is of the order of the distance between the groove edges, or smaller, the stripe-shaped sensor elements are centered along the edges of the grooves.

This provides the ability to analyze small amounts of a large number of different molecules or molecular fragments in parallel, in a short time. One biochip can hold for 1000 or more different molecular fragments. It is expected that the usefulness of information that can become available from the use of biochips will increase rapidly during the coming decade, as a result of projects such as the Human Genome Project, and follow-up studies on the functions of genes and proteins.

In case extremely large numbers of target species have to be analyzed, for instance from one fluid test sample, the substrates with the grooves can be stacked, forming a three dimensional array of channels. This allows a very compact detection system. Especially when the data processing occurs in the substrates stacked on each other.

Preferably the means for detecting a change in magnetoresistance of the magnetoresistive sensing devices comprise an integrated circuit. An electronic integrated circuit can easily be manufactured in the substrate. Especially when the substrate is a semiconductor, conventional techniques can be used to obtain electronic devices like MOSFET, bipolar transistors, diodes, optical devices or a variety of sensors such as temperature sensors, ion sensitive electrodes, pressure sensors, viscosity sensors, flow sensors and current sensors or voltage sensors.

It is another object of the present invention to provide a system that does allow for determination of the volume density in the fluid of the test sample.

The object of the invention regarding the system in accordance with the invention is achieved in that a magnetoresistive sensing device is used comprising a substrate with a layer structure for supporting a fluid, the layer structure having a first surface area in a first level and a second surface area in another second level and a magnetoresistive element for detecting the magnetic field of at least one magnetic particle in the fluid, the magnetoresistive element being positioned near a transition between the first and second surface area and facing at least one of the surface areas, and an electronic circuit for detecting a change in magnetoresistance of the magnetoresistive sensing devices, the electronic circuit being present in the substrate.

The electronic circuit may comprise a differential comparator circuit.

It is another object of the present invention to provide a method that does allow for determination of the volume density in the fluid of the test sample.

The object of the invention regarding the method in accordance with the invention is achieved in that a magnetoresistive sensing device is used comprising a substrate with a layer structure for supporting a fluid, the layer structure having a first surface area in a first level and a second surface area in another second level and a magnetoresistive element for detecting the magnetic field of at least one magnetic particle in the fluid, the magnetoresistive element being positioned near a transition between the first and second surface area and facing at least one of the surface areas, the method comprising the steps of providing a fluid comprising magnetic particles over the layer structure applying a magnetic field sensing the magnetoresistive sensing element, while applying the magnetic field comparing the output signal from the magnetoresistive sensing device to a reference signal taken at zero applied field to thereby determining the volume density of magnetic particles.

The volume density of magnetic nanoparticles is derived from the resistance change of the magnetoresistive sensing device upon the application of a perpendicular magnetic field, which follows from the change of the voltage difference over the device upon the application of the magnetic field when the sensor is operated at a constant sense current.

In general, it is required to determine independently the particle densities on the surfaces and in the bulk. This can be achieved by combining the measurements of several sensors integrated on the same chip or in the same device, the sensors having different surface structures, e.g. different values for $d_1$ and $d_2$. The data from an array of sensors can then be combined to yield accurate values of $\sigma_1$, $\sigma_2$ and N.

Equation (3) can be used for that purpose if the width of the magnetoresistive sensing element is much smaller than the distance d1 and d2. This is generally not the case, since the width of the sensing element can be of the same magnitude as the distance d1 and d2. The derived equations are therefore just to illustrate the principle of the invention.

If the area1 densities are equal $\sigma_1=\sigma_2$, the volume density N is proportional to the difference in resistance between a first magnetoresistive sensing element corresponding to a first surface structure and a second sensing element corresponding to a second surface structure having a third and fourth surface level, if $(1/d1-1/d2)=(1/d3-1/d4)$ and d2/d1 is not equal to d4/d3. The distances d3 and d4 being the distance of the second sensing element to the third and fourth surface respectively.

If the area1 densities are not equal: $\sigma_1=/\sigma_2$, a third sensing is necessary. For example d6/d5 is equal to d2/d1, but d6, (d5) is not equal to d1,(d2) respectively. From the difference in resistance values between the sensing elements sensoren with d1/d2 en d5/d6 follows $(\sigma_1/d1-\sigma_2/d2)$, so the measured magnetic field of the d1/d2 sensor can be corrected.

These and other features and advantages of the device according to the invention will become apparent from the following detailed description, taken in conjunction with the accompanying drawings, which illustrate, by way of example, the principles of the invention. This description is given for the sake of example only, without limiting the scope of the invention.

The reference figures quoted below refer to the attached drawings. Therein is.

Figure 1:
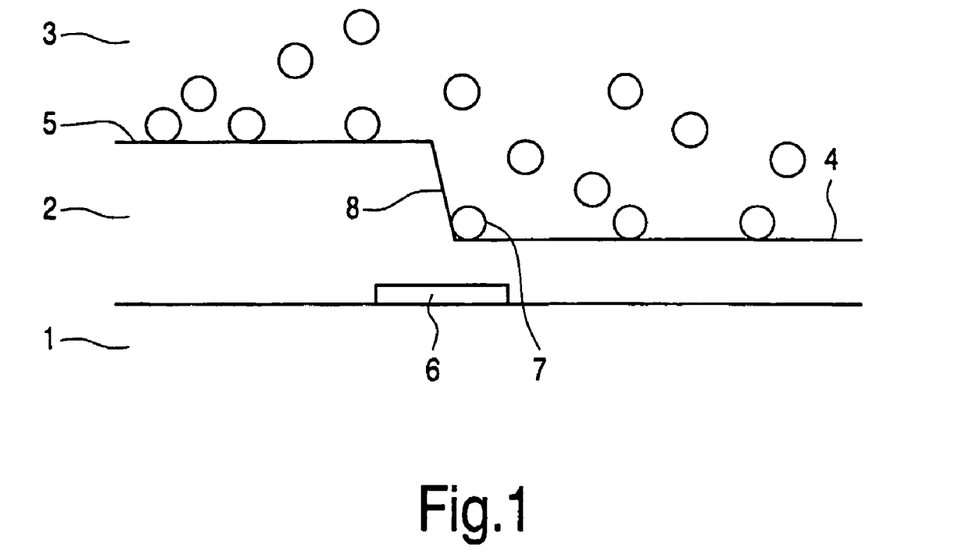
FIG. 1 a schematic cross sectional view of the magnetoresistive sensing device according to the invention.

The magnetoresistive sensing device in FIG. 1 comprises a substrate (1) with a layer structure (2) for supporting a fluid (3). The layer structure has a first surface area (4) in a first level and a second surface area (5) in another second level and a magnetoresistive element (6) for detecting the magnetic field of at least one magnetic particle (7) in the fluid (3). The magnetoresistive element (6) has been positioned near a transition (8) between the first and second surface area and facing at least one of the surface areas (4,5).

The fluid comprises a target molecule species or an antigen.

Any biological molecule that can have a magnetical label can be of potential use in this application.

Figure 2:
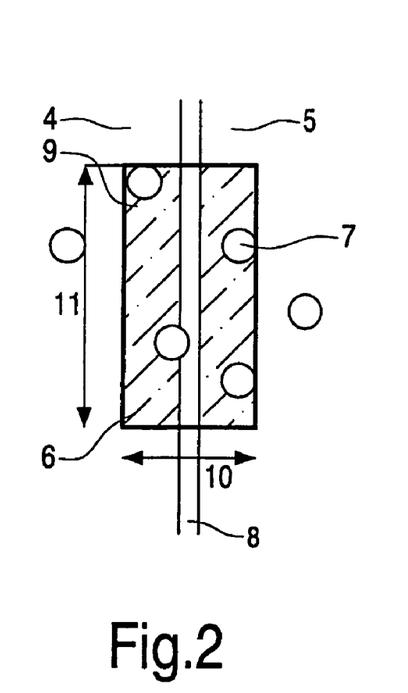
FIG. 2 a schematic top view of the magnetoresistive sensing device according to the invention.

In FIG. 2 the width 10 and length 11 of the magnetoresistive (MR) sensor element is much larger than the diameter of the magnetic nanoparticles of which the presence and concentration is to be measured.

The nanoparticles may for example have a diameter between 1 and 250 nm, preferably between 3 and 100 nm, most preferred between 10 and 60 nm. For such small particles, the diffusion is fast. The width and length dimensions of sensor elements are at least a factor 10 or more, preferably a factor 100 or more, larger than the diameter of the nanoparticles, for example 1 μm×1 μm. Other dimensions for the sensor elements are also possible. If different dimensions are used, different S/N ratios are obtained.

The magnetoresistive sensing element 6 comprises thin film materials, in the example under reference GMR materials, but also other thin film materials such as AMR, TMR or other MR materials with substantially linear R(H) curves around H=0 are possible materials. The sensing element is separated from the magnetic nanoparticles 7 by a layer e.g. silicon dioxide, silicon nitride, or an organic material such as a resist or epoxy for example.

Figure 3:
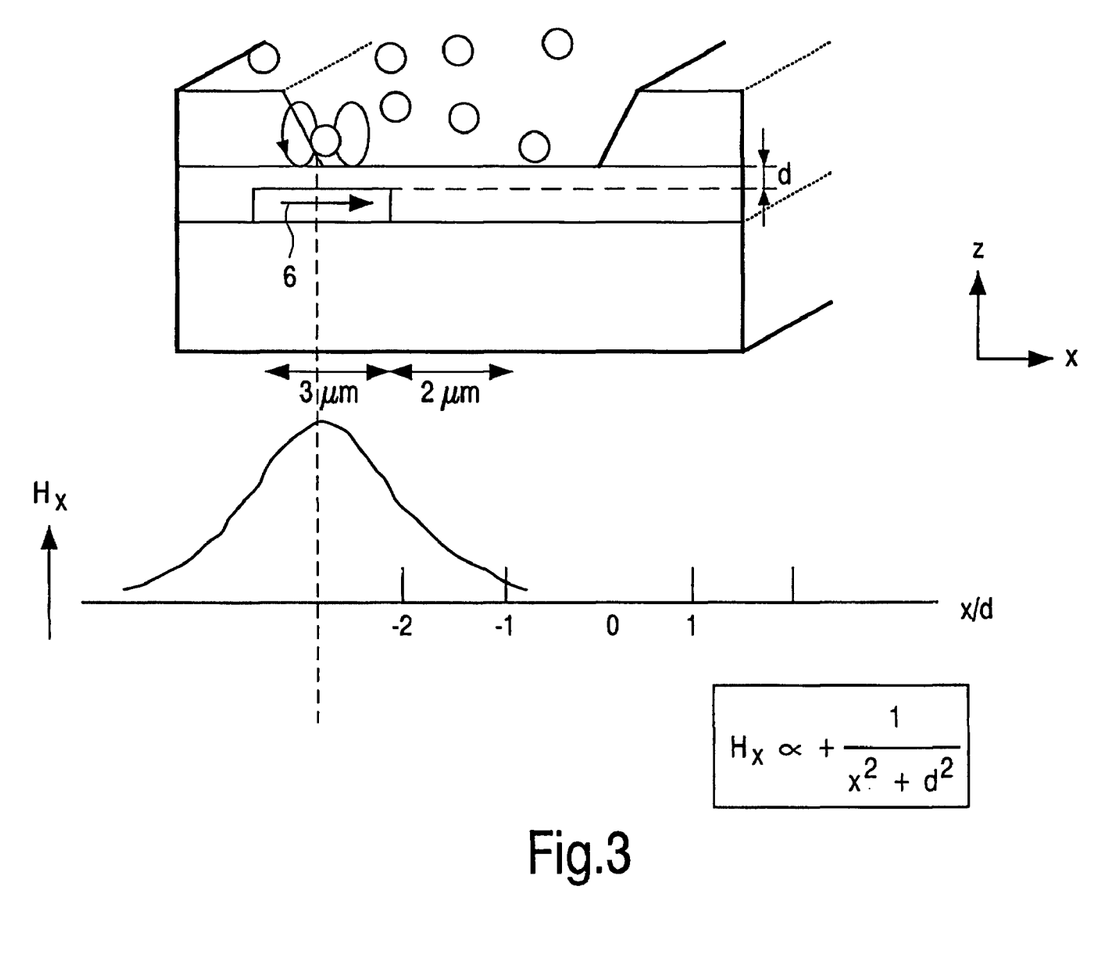
FIG. 3 a graph illustrating the x-component of the magnetic field of the nanoparticles in the plane of a GMR sensing element.

In a first embodiment of the magnetoresistive sensing device, the magnetoresistive sensing element consists of a GMR strip. The GMR strip of the sensing element can be a meander, resulting in a larger area and improved sensitivity. If a magnetic field is applied perpendicular to the magnetoresistive sensing element 6, there is a fringing field at the transition between the first and the second surface area of the layer structure. In FIG. 3 is shown that the magnetic field in the x-direction of the sensing element is largest if the center of the sensing element is below the center of the transition 8.

Figure 4:
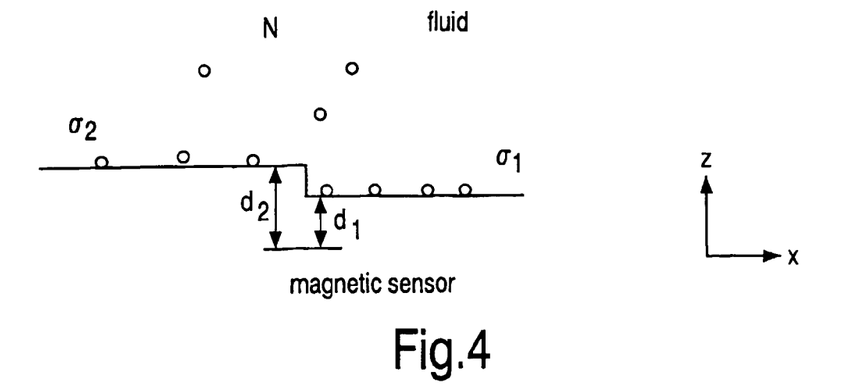
FIG. 4 Schematic cross-section of the magnetoresistive sensing device, having a volume density and area1 densities of magnetic particles.

The magnetisation of the nanoparticles 7 is controlled by an external field applied perpendicular to the magnetoresistive element (i.e. along the z-axis) as shown in FIG. 4. The magnetoresistive element is now exposed to the magnetic field resulting from the nanoparticles 7.

For a particle magnetisation along the positive z-direction, the in-plane magnetic field below a step-like transition between the first and second surface area can to first order be approximated by:

$$H_x \approx +\frac{m}{2\pi}\left[\frac{\sigma_1}{d_1} - \frac{\sigma_2}{d_2} + N \ln\left(\frac{d_2}{d_1}\right)\right]$$

with m the magnetic moment of the particle. The areal density of the magnetic nanoparticles 7 on the first surface area is given by density $\sigma_1$, and on the second surface area by density $\sigma_2$. The volume density of magnetic nanoparticles 7 in the fluid containing the with nanoparticles 7 labeled elements is given by N.

Figure 5:
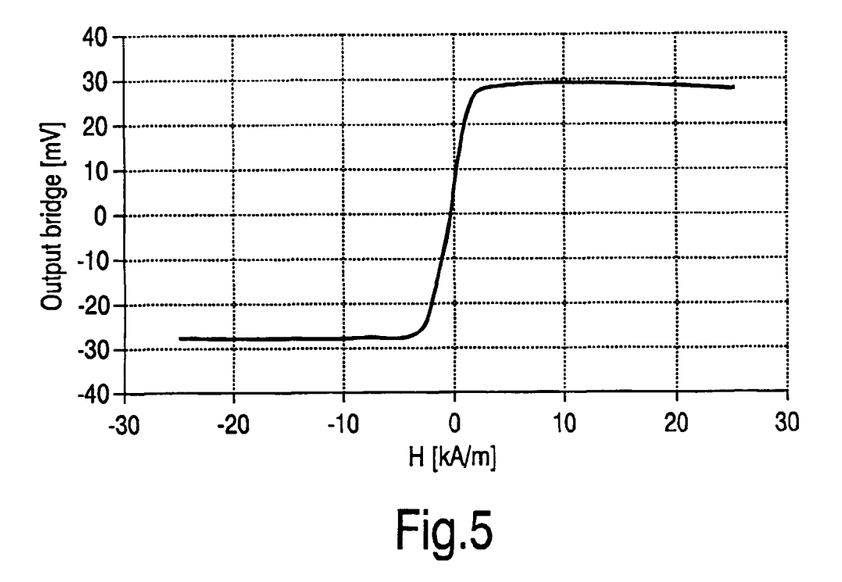
FIG. 5 a graph of the response of a multilayer GMR sensor element to an applied field according to the present invention.

In the special case that the areal density is almost zero, the density N of magnetic particles is derived from the resistance of the sensing element. A typical output signal from the magnetoresistive element 6 is shown in FIG. 5. The concentration N is determined from the value of the magnetic field $H_x$, the known magnetic moment of a magnetic particle with a diameter of 35 nm being m=3.10$^{18}$ Am$^2$, and the distance d1, d2 and the formula $$H_x \approx +\frac{m}{2\pi}\left[N \ln\left(\frac{d_2}{d_1}\right)\right].$$

Figure 6:
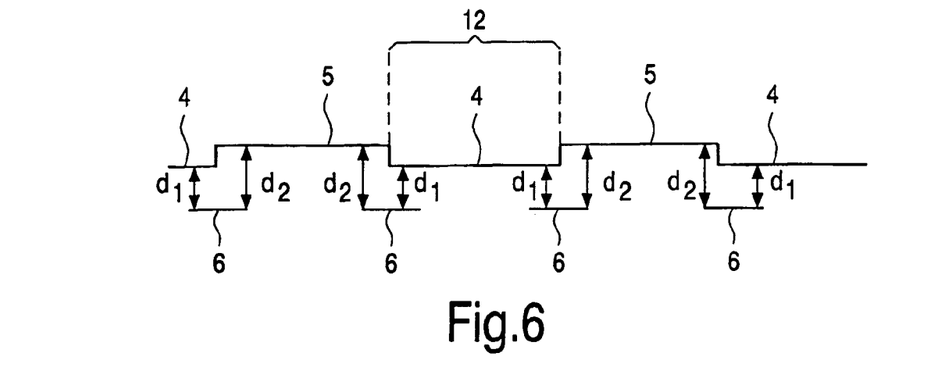
FIG. 6 schematically shows a multi-step structure above a plurality of magnetic sensor elements.

FIG. 6 shows a multiple step structure and many sensing elements. Over a large area the volume density can be determined.

Figure 7:
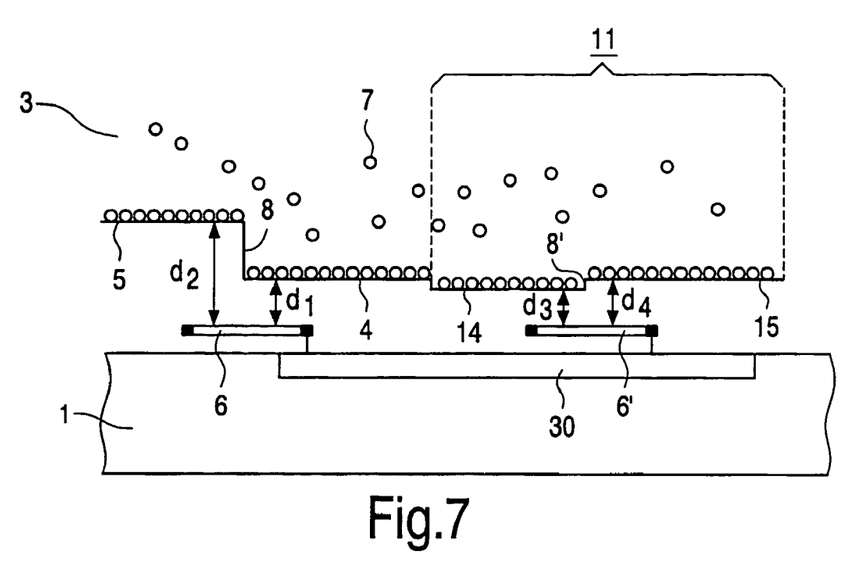
FIG. 7 a schematic cross sectional view of the system according to the invention.

In FIG. 7 a structure is shown which has many levels on top of the substrate. This structure is useful for the determination of uniform areal density. In addition to the physical structure, the first and second surface areas can also be chemically structured. For instance the surface of the layer structure is plasma polymerized. For instance PEGs (polyethylene) are provided uniformly on the surface. Capture molecules can for example be antibodies, antibody fragments, receptors, ligands, nucleic acids or oligonucleotides. The capture molecules are chemically or physical-chemically provided over the surface. These capture molecules are able to selectively bind a target.

The volume density N can be determined from the difference of the output signals of the magnetoresistive sensing elements 6 and 6'.

In the special case that 1/d1−1/d2=1/d3−1/d4, the difference of the signal yields −m/2π·N(ln d2/d1−ln d4/d3). From the known distances to the surfaces, the volume concentration N is determined. For example the distances can be d1=1 μm, d2=2 μm, and d3=2/3 μm, d4=1 μm.

The output signals from the magnetoresistive sensing elements can be amplified, for instance with a differential amplifier. In the semiconductor substrate 1, there are many semiconductor devices present which form an electronic circuit 30, such as bipolar transistors, mosfets and diodes.

In an advantageous method, a magnetic field is applied perpendicular to the magnetoresistive sensing elements. The magnetic field has a magnitude of typically 100–1000 Oe and is switched.

In a first step the uniformity of the magnetic field is optimized. At a time t1=0 the current through the coil or coils is registered. The magnetoresistance value of the sensing elements are registered. At a second time t2, the magnetoresistance curve of the sensing elements 6 and 6' is detected again. If there is a large difference between the output R(H) curves of the sensing elements 6 and 6' between t1=0 and t2, this indicates that the position of the particles is changed due to the force on the particles that results from a field gradient. The magnetic field must then be tuned, for instance with small coils which yield a compensation field gradient.

Having a uniform magnetic field, the magnetic field is on during a typical time of 1 ms. During this time the magnetoresistive sensing elements 6 and 6' are sensed by sending a current through the devices. From the difference in output signals the volume density and area1 density is determined. It is of large importance to have the output signals of the magnetoresistive sensing elements at zero magnetic field as a reference. The reference resistance values are determined with a lock-in technique. It is also possible to measure for instance during 1 ms at zero magnetic field, 1 ms at a magnetic field H and again 1 ms at zero magnetic field to obtain a reference.

When the magnetic field is off, the relaxation is very fast and occurs almost immediately. This relaxation time is much smaller than 1 ms. During the time the magnetic field is switched off, the magnetic particles diffuse very rapidly. The diffusion length is much larger than the distance over which the magnetic particles attract each other. In 1 ms, the diffusion distance of a magnetic particle with a diameter of 35 nm is about 0.15 micrometer, while the distance of attraction for a volume density of 1 nmol/l is about 10 picometer for a particle with a magnetic moment $m=3.10^{18}$ $Am^2$.

During the off-time, a uniform distribution of magnetic particles is reached. The time the magnetic field is off is typical 1 ms. In several areas of the sample can be measured as a function of time.

During a time of 3 minutes, at least 100 measurements can be done.

With this procedure, the accuracy with which the volume concentration can be detected is at least 1 nmol/l. The area1 particle density typically ranges between zero and $10^3$ to $10^4$ particles per $\mu m^2$.

In order to determine the volume density as well as the area1 density, a second layer structure is present as shown in FIG. 7. The second layer structure has a third surface area in a third level and a fourth surface area in a fourth level.

The second layer structure corresponding a second magnetoresistive element being positioned near a transition between the third and fourth surface area and facing at least the third surface area.

From equation (3) it can be derived that in case of an uniform area1 density $\sigma_1 = \sigma_2$, the distance from the magnetoresistive sensing elements to the surface must be $1/d1 - 1/d2 = 1/d3 - 1/d4.$ The difference in magnetic field $H_{x1} - H_{x2} = -m/2\pi \cdot N$ (ln d2/d1−ln d4/d3).

From the difference in magnetoresistance and the known R(H) characteristic, the volume density can be extracted. From the magnetoresistance signal of the first Wheatstone bridge, the area1 density can be determined.

Figure 8:
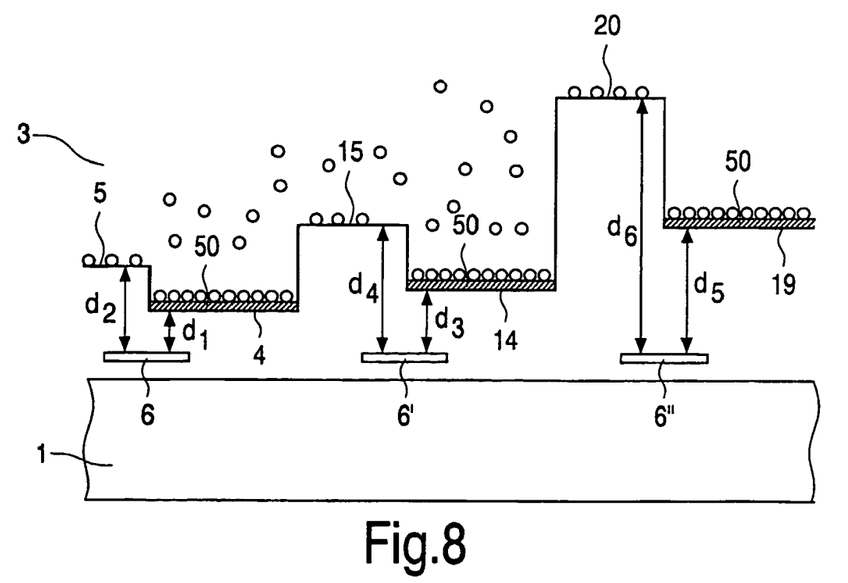
FIG. 8 schematically shows a cross sectional view of a layer structure, with surface areas in the first to sixth level.

From FIG. 8 and equation (3) it can be derived that in case of an area1 density whereby $\sigma_1 \neq \sigma_2$, the distance from the magnetoresistive sensing elements to the surface must be:

$1/d1 = 1/d3 + 1/d5$ $1/d2 = 1/d4 + 1/d6$ and $d1 \neq d2$, $d3 \neq d4$ and $d5 \neq d6$ The difference in magnetic field $H_{x1} - H_{x2} - H_{x3} = m/2\pi \cdot N$ (ln d1/d2−ln d4/d3−ln d6/d5).

From the difference in magnetoresistance and the known R(H) characteristic, the volume density can be extracted. From the magnetoresistance signal of the first and second Wheatstone bridge, the area1 density $\sigma_1$, and $\sigma_2$ can be determined.

The invention claimed is:

1. A magnetoresistive sensing device, comprising a substrate with a layer structure for supporting a fluid, the layer structure having a first surface area in a first level and a second surface area in another second level and a magnetoresistive element for detecting the magnetic field of at least one magnetic particle in the fluid, the magnetoresistive element being, as seen in substantially perpendicular projection, centered around a transition between the first and second surface area and facing at least one of the surface areas.

2. A magnetoresistive sensing device according to claim 1, wherein there is an overlap between the magnetoresistive sensing element and the first surface area in the case of a substantially perpendicular projection of the first and second surface areas on the magnetoresistive sensing element.

3. A magnetoresistive sensing device according to claim 1, wherein the transition has a step-like profile.

4. A magnetorsistive sensing device according to claim 1, wherein the magnetoresistive sensing device has a Wheatstone bridge configuration comprising magnetoresistive elements being positioned on the substrate.

5. A magnetorsistive sensing device according to claim 1, wherein a second layer structure is present, the second layer structure having a third surface area in a third level and a fourth surface area in a fourth level, and to the second layer structure corresponding a second magnetoresistive element being positioned near a transition between the third and fourth surface area and facing at least the third surface area.

6. A magnetorsistive sensing device according to claim 1, wherein the magnetoresistive element is present on the substrate.

7. A magnetoresistive sensing device, comprising a substrate with a layer structure for supporting a fluid, the layer structure having a first surface area in a first level and a second surface area in another second level and a magnetoresistive element for detecting the magnetic field of at least one magnetic particle in the fluid, the magnetoresistive element being positioned near a transition between the first and second surface area and facing at least one of the surface areas, wherein the structured surface is formed by a plurality of grooves positioned parallel to each other.

8. A magnetorsistive sensing device according to claim 7, wherein structured surfaces are stacked on top of each other, forming a three dimensional array of channels.

9. A system for determining a density of magnetic particles in a fluid, the system comprising the magnetorsistive sensing device according to claim 1.

10. A system according to claim 9, further comprising an electronic circuit for detecting a change in magnetoresistance of the magnetoresistive sensing devices, the electronic circuit being present in the substrate.

11. A system according to claim 9, further comprising means for generating a magnetic field.

12. A method for determining the density of magnetic particles in a fluid using the device of claim 1, the method comprising the steps of providing a fluid comprising magnetic particles over the layer structure applying a magnetic field sensing the magnetoresistive sensing element, while applying the magnetic field comparing the output signal from the magnetoresistive sensing element to a reference signal obtained in the absence of an applied field to thereby determining the volume density of magnetic particles.

13. A method according to claim 12, comprising the steps of: sensing a second magnetoresistive element corresponding to a further second layer structure having, the further layer structure having a third surface area in a third level and a fourth surface area in a fourth level compare the output signals from the magnetoresistive sensing elements corresponding to the first and second layer structures, and compare these signals to the signals determined in the absence of an applied field, to thereby determine the volume density and areal density of magnetic particles.

14. A method according to claim 13, comprising the steps of: providing a probe area having a binding site on the first surface of the layer structure before providing the fluid, sensing a third magnetoresistive element corresponding to a further third layer structure, the further third layer structure having a fifth surface area in the fifth level and a sixth surface area in a sixth level, and comparing the output signals from the magnetoresistive sensing devices corresponding to the first, second and third layer structures with and without the applied field, to thereby determine the volume density, the areal density of magnetic particles present on the second surface and the areal density of magnetic particles present in the probe area on the first surface.

15. A method according to claim 12, wherein the fluid is blood.

16. A method according to claim 12, wherein the fluid is urine.

17. A method of detecting a concentration of magnetic particles coupled to a target in a fluid, making use of the magnetoresistive sensing device as claimed in claim 1, the method comprising the steps of: providing a fluid comprising the target over the layer structure applying a magnetic field sensing the magnetoresistive sensing element, while applying the magnetic field comparing the output signal from the magnetoresistive sensing element to a reference signal obtained in the absence of an applied field to thereby determining the volume density of magnetic particles.

18. A method as claimed in claim 17, wherein the fluid is one of blood and urine.

19. A system as claimed in claim 9, wherein the system is a blood tester.

* * * * *